United States Patent [19]

Thomas et al.

[11] Patent Number: 5,409,463
[45] Date of Patent: Apr. 25, 1995

[54] CATHETER INTRODUCER WITH LUBRICATION MEANS

[75] Inventors: Joseph J. Thomas, Berwyn; Robert W. Thomas, Wayne; David G. Catlin, West Chester; Andrew W. Armour, Springfield, all of Pa.

[73] Assignee: Thomas Medical Products, Inc., Malvern, Pa.

[21] Appl. No.: 132,680

[22] Filed: Oct. 6, 1993

Related U.S. Application Data

[63] Continuation of Ser. No. 893,870, Jun. 5, 1992, abandoned.

[51] Int. Cl.6 .................................................. A61M 5/178
[52] U.S. Cl. .................................. 604/167; 604/164; 604/280
[58] Field of Search ............... 604/164, 167, 170–172, 604/280; 137/849

[56] References Cited

U.S. PATENT DOCUMENTS

| 4,475,598 | 10/1984 | Muto | 604/167 |
| 4,798,594 | 1/1989 | Hillstead | 604/167 |
| 4,929,235 | 5/1990 | Merry et al. | 604/167 |
| 5,098,393 | 3/1992 | Amplatz et al. | 604/164 |
| 5,104,389 | 4/1992 | Deem et al. | 604/167 |

*Primary Examiner*—Randall L. Green
*Assistant Examiner*—Rob Clarke
*Attorney, Agent, or Firm*—Caesar, Rivise, Bernstein, Cohen & Pokotilow, Ltd.

[57] ABSTRACT

Apparatus for introducing a catheter percutaneously into the body of a living being. The apparatus comprises a tubular member having a distal end portion and a proximal end portion. The proximal end portion is in the form of a hollow housing for a hemostatic valve assembly comprising a lubricant reservoir and a valve element. The reservoir is formed of a foam material impregnated with a lubricant liquid, e.g., silicone. The valve element is a disk-like member formed of resilient material, e.g., silicone impregnated with polydimethylsiloxane, located distally of the reservoir and has a openable passageway extending through it for the catheter to pass. The reservoir applies the lubricating fluid in a controlled manner onto the catheter as it is passed through it, to thereby facilitate the passage of the catheter through the openable passageway in the valve element. The hollow housing is arranged to produce peripheral pressure on the valve element to facilitate its closure.

13 Claims, 1 Drawing Sheet

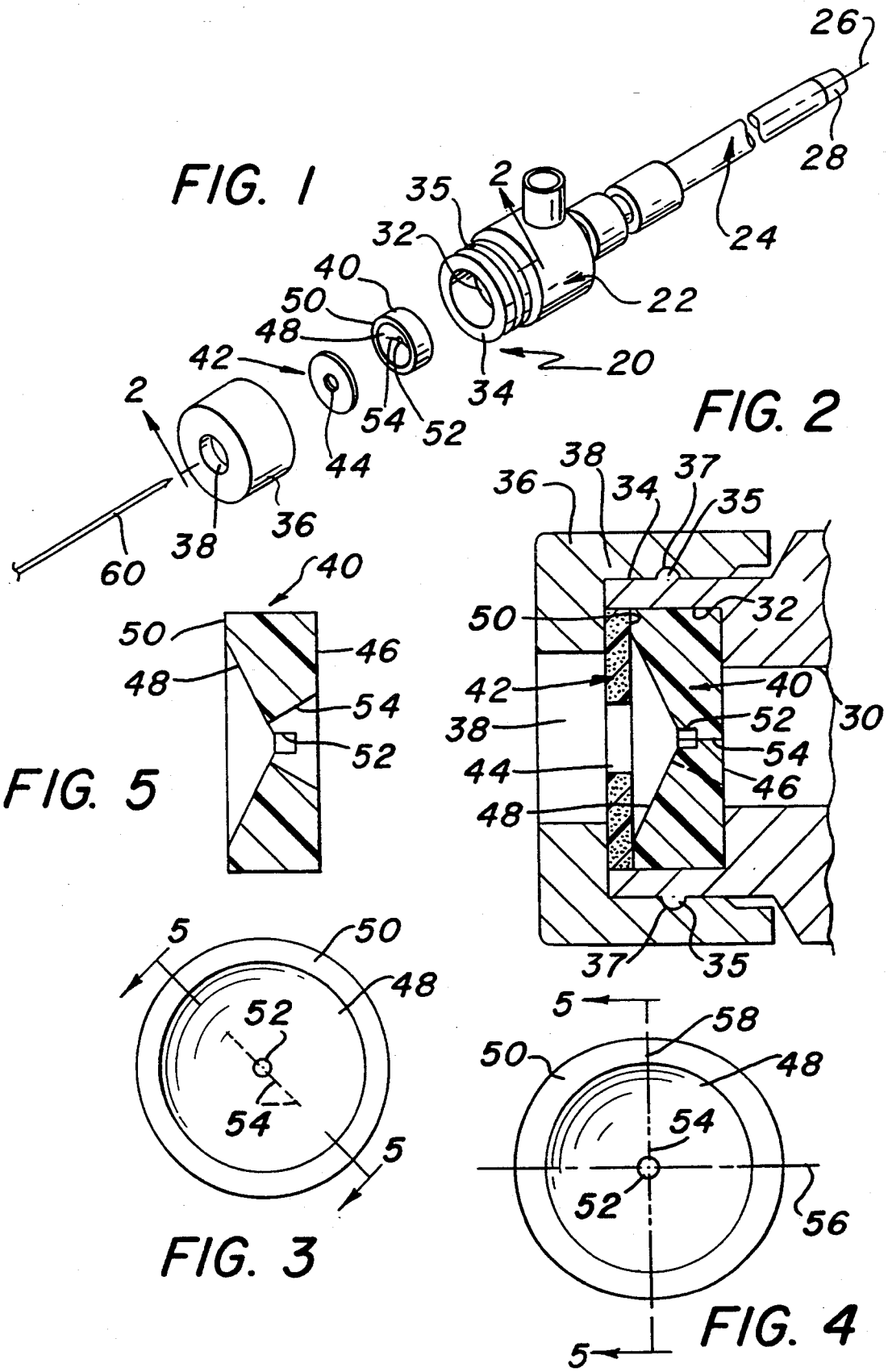

CATHETER INTRODUCER WITH LUBRICATION MEANS

This application is a continuation of application Ser. No. 07/893,870, filed Jun. 5, 1992, now abandoned.

BACKGROUND OF THE INVENTION

This invention relates generally to medical devices and more particularly to devices for introducing a catheter or other elongated instrument into the body of a living being via a percutaneous incision or puncture.

Various introducer devices are disclosed in the patent literature and many are commercially available for effecting the introduction of a catheter or some other instrument through a percutaneous incision or puncture into the body, e.g., an artery, of a living being. Such devices commonly make use of some hemostatic valve mechanism to ensure that blood does not flow out of the introducer when it is in place. Examples of such devices are found in the following U.S. Pat. Nos.: 3,459,183 (Ring et al), 4,000,739 (Stevens), 4,424,833 (Spector et al), 4,430,181 (Timmermans), 4,610,665 (Matsumoto et al) 4,610,674 (Suzuki et al), 4,626,245 (Weinstein), 4,655,752 (Honkanen et al), 4,723,550 (Boles et al), 4,726,374 (Boles et al), 4,874,378 (Hillstead), 4,895,565 (Hillstead), 4,929,235 (Merry et al), and 5,000,745 (Guest et al). The valve mechanisms used in such device typically comprise one or more valve components formed of an elastomeric material having one or more slits or apertures therein to enable a catheter or some other instrument to be inserted therethrough, with the slit(s) or aperture(s) sealing closed after the catheter or instrument has been removed therefrom. The elastomeric materials making up the prior art valve components typically exhibit a relatively high coefficient of friction. Thus, prior art introducers have tended to be somewhat resistant to the easy passage of a catheter or other instrument therethrough. In order to facilitate the passage of the instrument through prior art valve members, i.e., to reduce the friction therethrough, some prior art introducers utilize fluid lubricants, e.g. silicone, impregnated in the material making up the valve member.

While such prior art devices are generally suitable for their intended purposes they never the less still leave something to be desired from the standpoints of facilitating the introduction of delicate instruments therethrough, while ensuring that a good hemostatic seal exists to prevent the outflow of blood from the introducer.

OBJECTS OF THE INVENTION

Accordingly, it is a general object of this invention to provide a catheter introduction valve which overcomes disadvantages of the prior art.

It is a further object of this invention to provide a catheter introduction valve which enables a catheter to be readily extended therethrough while precluding blood from flowing out of the valve.

It is still a further object of this invention to provide a catheter introduction valve which facilitates ease of insertion and precise placement of catheters or other similar devices within the body of a living being.

It is still a further object of this invention to provide a catheter introduction valve which is non-damaging to delicate catheter based instruments or devices passed therethrough into the body of a living being.

It is yet a further object of this invention to provide a catheter introduction valve which is simple in construction.

SUMMARY OF THE INVENTION

These and other objects of this invention are achieved by providing an apparatus for introducing an elongated device, e.g., a catheter, percutaneously into the body of a living being. The apparatus comprises a tubular member having a distal end portion and a proximal end portion. The proximal end portion is in the form of a hollow housing in which hemostatic valve means is located. The hemostatic valve means comprises reservoir means and a valve element.

The reservoir means has an opening through which the elongated device may pass and is formed of a foam material impregnated with a lubricant liquid, e.g., silicone. The valve element is located distally of the reservoir means and has a openable passageway extending through it for the device to pass. The reservoir means is operative to provide the lubricating fluid onto the elongated device as it is passes therethrough to facilitate the passage of the elongated device through the openable passageway in the valve element.

DESCRIPTION OF THE DRAWINGS

Other objects and many attendant features of this invention will become readily appreciated as the same becomes better understood by reference to the following detailed description when considered in connection with the accompanying drawings wherein:

FIG. 1 is an exploded isometric view of a catheter introducer apparatus constructed in accordance with this invention;

FIG. 2 is an enlarged sectional view taken along lines 2—2 of FIG. 1;

FIG. 3 is a plan view of one embodiment of a valve located within the apparatus shown in FIG. 2;

FIG. 4 is a plan view of another embodiment of a valve located within the apparatus shown in FIG. 2; and FIG. 5 is a sectional view taken along lines 5—5 of FIGS. 3 and 4.

DETAILED DESCRIPTION OF THE PREFERRED EMBODIMENTS

Referring now to the various figures of the drawing wherein like reference characters refer to like parts, there is shown at 20 in FIG. 1, a catheter introduction valve apparatus constructed in accordance with this invention. The apparatus 20 basically comprises hollow housing or body 22 from which a sheath 24 extends. The sheath is an elongated tubular member of any suitable size, and has a longitudinal central axis 26. The distal end 28 of the sheath is in the form of an open tip. The sheath is arranged to be inserted through a percutaneous incision or puncture into the body, e.g., the vascular system, of a living being so that some instrument, e.g., a catheter on a guidewire, can be passed therethrough to effect some procedure therein. To that end the sheath includes a central passageway or bore (not shown) extending its entire length from a point at the proximal end thereof to the open tip 28.

The body 22 includes a central bore 30 at the distal end thereof which is in communication with the central passageway in the sheath 24. A hollow circular chamber 32 is located contiguous with the central bore and coaxial with the central longitudinal axis 26 so that it is in fluid communication with the passageway through the sheath 24. The proximal end of the body includes a portion 34 having an annular bead or ridge 35 (FIG. 2) extending about the periphery thereof. A cap 36, having an annular recess 37 for receipt of the ridge 35, serves to close the proximal end 34 of the body. The cap 36 is secured to the body by any suitable adhesive, e.g., cyanoacrylate, and includes a central opening or port 38 located centered on the longitudinal axis to provide an entrance port for the introduction of a device, e.g., guide-wire, dilator, balloon catheter, etc., therethrough.

In order to ensure that blood does not flow out of the apparatus 20 when its sheath 24 is in position within the patient's body, it includes hemostatic valve means located within the hollow interior chamber 32 of the housing body 22. That means basically comprises a valve element 40 and a lubrication reservoir element 42. The valve element 40 will be described in detail later. Suffice it for now to state that the valve element includes an openable passageway through which the devices, e.g., guide-wire, dilator, catheter, etc., which are to be introduced through the apparatus 20 may pass. When any such device is extended through the valve element the valve's passageway closes relatively tightly about the periphery of the device to preclude blood from flowing through the interface therebetween and hence out of the apparatus, while enabling the device to be readily slid longitudinally along the axis 26. The valve's passageway is arranged to close completely, i.e., close on itself, when no device extends through it.

The reservoir element 42 will also be described in detail later. Suffice it for now to state that the reservoir element 42 basically comprises a washer-like member having a central hole 44 through which the device(s) to be introduced is(are) arranged to pass. The reservoir element 42 serves to facilitate the passage of a device through the valve element 40 by applying a lubricating liquid to the exterior of that device. This feature is of considerable importance when the apparatus 20 is used to introduce a relatively delicate device, e.g., a balloon catheter, therethrough, since it enables the device to pass readily through the valve element, while maintaining hemostasis.

In accordance with a preferred embodiment of this invention the reservoir member 42 is formed of a foam, e.g., urethane foam, and which has been vacuum soaked in a suitable lubricant liquid, e.g., medical-grade silicone, so that it may apply the lubricant liquid in a controlled even manner to the surface of the device, e.g., balloon catheter, as it is slid therethrough. To that end the internal diameter of the hole 44 in the reservoir member 42 is selected to be smaller than the outside diameter of the instrument, e.g., balloon catheter, to be introduced by the apparatus 20 so the lubricant in the reservoir is dispensed, i.e., wiped, in a controlled manner on the exterior surface of the catheter as it is passes through the opening 44.

The valve element 40 is disposed within the hollow chamber 32 in the body 22 immediately distally of the reservoir element 42. The valve element 40 can take various forms. For example one embodiment of the valve element 40 is best seen in FIGS. 1, 2, 3 and 5 and basically comprises a circular, disk-like member formed of a resilient material, e.g., silicone, having a planar distal face 46 and a concave proximal face made up of a conical surface 48 located centrally within a circular, planar surface 50.

A central bore 52 extends into the valve element 40 at the nadir of the conical surface 48. The bore 52 is circular and has an inner diameter which is less than the outer diameter of the guide-wire which is used to position the introducer element at the desired position within the body of the patient (as will be described later). A planar, normally closed, slit 54 of a predetermined length is located coaxially with the central axis 26 of the introducer apparatus 20 and extends fully through the portion of the valve element 40 between the conical surface 48 closely adjacent the bore 52 and the planar distal face 46. As can be seen clearly in FIGS. 3 and 5 the slit 54 is flared outward from the conical surface 48 to the planar distal face 46, e.g., it is 0.08 inch (2.03 mm) at the conical surface and is 0.15 inch (3.81 mm) wide at the planar distal face. The bore 52 and cooperating slit 54 make up the heretofore mentioned passageway in the valve element 40.

By virtue of the resilient material making up the valve element 40 the slit 54 is openable to allows passage of the catheter therethrough without blood leakage at the interface. In a similar manner the bore 52 prevents blood leakage around the guide-wire when it is extended through the valve element. When the valve element is free of inserted devices, e.g., the guidewire, catheter, etc., the slit 54 automatically closes on itself, i.e., the edges forming the slit abut each other, thereby precluding the outflow of blood through the introducer apparatus 20.

In accordance with a preferred embodiment of this invention the valve element 40 is molded of a silicone, and is processed by soaking it in polydimethylsiloxane fluid to allow it to expand in excess of ten (10) percent. This procedure impregnates the silicone of the valve element to render it self-lubricating. In addition the polydimethylsiloxane renders the silicone more pliable. Both of these effects are desirable to facilitate the passage of the catheter therethrough. Moreover, the expansion of the silicone valve element ensures that when it is located within the cylindrical hollow interior of the housing body 22 a substantial amount of pressure is applied uniformly about the periphery of the valve element to ensure that the bore portion of passageway closes hemostatically about the device, e.g., catheter, passing therethrough, and to ensure that the slit portion of the passageway closes completely once that device is removed.

In FIGS. 4 and 5 there is shown an alternative embodiment 40' of the valve of this invention. The 40' is in all material respects identical to the valve 40' described heretofore, except that the valve element is not circular in shape so that radial force applied to it by the inner wall of the chamber 32 is concentrated at selected portions on the periphery of the valve to facilitate the hemostatic closure of its slit 54. In particular, the periphery of the valve element 40' is of an oval shape, e.g., is 0.28 inch (7.11 mm) along its major axis 56 (FIG. 4) and 0.26 inch (6.6 mm) along its minor axis 58. The conical surface 48 of the valve element 40' is circular of 0.225 inch (5.72 mm) diameter. The slit 52 is identical to that of valve 40 and is oriented so that it extends perpendicular to the major axis 56. Thus, when the valve element 40' is located within the circular housing chamber 32, higher radial compressive forces will be applied along the major axis on each side of the slit 54 as compared to the radial compressive force applied along the minor axis to the ends of the slit. Obviously, such action will expedite the secure closure of the slit 54 once all instruments or devices have been removed therefrom.

It should be pointed out at this juncture and appreciated by those skilled in the art that in lieu of utilizing an oval valve element 40' within a circular housing chamber 32, the valve element may be circular, like valve element 40, with the chamber 32 being oval. In such a case the valve element 40 should be oriented within the oval chamber so that the slit 52 is perpendicular to the major axis of the oval chamber, whereupon the compressive forces will be concentrated on the sides of the slit and not its ends.

The introduction of the apparatus 20 into an artery is as follows. A conventional guide wire 60 (FIG. 1) is introduced into the patient's artery via an appropriate percutaneous incision or puncture. Once the guide-wire is in place the introducer apparatus 20 of this invention is placed on a conventional dilator (not shown), or a specially designed dilator (not shown), and together they are slid down the guide wire so that the percutaneous incision or puncture is held open by the dilator. The introducer apparatus 20 on the dilator is then slid down the dilator until its distal end 28 is located at the desired situs within the artery. Blood from within the artery is precluded from gaining egress out of the introducer apparatus 20 during the placement thereof by virtue of the fact that the bore portion 52 of the valve element 40 stretches slightly about the periphery of the dilator as the introducer is slid down the dilator into position. After the introducer is in position the dilator can then be removed by sliding it out of the introducer apparatus 20.

After the dilator is removed the bore portion 52 of the valve element closes in radially on the guidewire 60 to hemostatically engages its periphery. The introducer apparatus 20 is now ready to accept any suitable instrument to effect its intravascular placement. Thus, for example any conventional catheter (not shown), whose diameter is substantially larger than that of the guide-wire, can be slid onto the guide-wire for passage through the introducer body 22, whereupon the reservoir member 42 deposits the lubrication liquid on the periphery of the catheter, thereby enabling it to pass easily through the bore portion 52 and the slit portion 54 of the valve element 40 or 40', down the passageway in the sheath 24 and out its open end 28 into the artery. Blood from within the artery is precluded from gaining egress out of the proximal end of the introducer apparatus 20 during the placement of the catheter by virtue of the fact that the bore portion 52 of the valve element 40 or 40' stretches slightly to hemostatically engage the periphery of the catheter as it is slid down the guide wire into position. This hemostatic seal is maintained all the while that the catheter is extended through the introducer apparatus.

When it is desired to remove the catheter all that is required is to retract it, i.e., pull it proximally. Once the distal end of the catheter passes through, i.e., clears, the valve element, the bore portion 52 of the valve element 40 or 40' closes inward radially to form a hemostatic interface about the periphery of the guide-wire 60 still extending therethrough. The catheter can then be fully withdrawn from the introducer apparatus 20, without any blood exiting therefrom. The guidewire can then be removed, if desired. To that end the guide-wire can be retracted in the proximal direction. Once the free end of the guide-wire clears the slit 54 of the valve element 40 or 40', the slit 54 immediately closes, whereupon blood from within the artery is precluded from passing through the valve element. The guide-wire 60 can then be completely withdrawn from the introducer apparatus 20, and the apparatus left in place for any reason desired, e.g., to serve as an entranceway for some other instrument, all the while precluding blood from flowing out of it.

As should be appreciated from the foregoing the catheter introduction apparatus of the subject invention is simple in construction, very easy to use, and by virtue of its controlled application of lubrication to devices passing therethrough is gentle and non-damaging to delicate devices, such as commonly used in vascular and other similar procedures, all the while being very effective to establish complete hemostasis.

Without further elaboration, the foregoing will so fully illustrate our invention that others may, be applying current or future knowledge, adopt the same for use under various conditions of service.

We claim:

1. Apparatus for introducing an elongated device percutaneously into the body of a living being, said apparatus comprising a tubular member having a distal and proximal end portion, said proximal end portion comprising a hollow housing in which hemostatic valve means is located, said hollow housing including a portion of circular shape, said hemostatic valve means comprising reservoir means and a valve element having an oval periphery, said reservoir means having an opening therein through which said elongated device may pass and being formed of a foam material impregnated with a lubricant liquid, said valve element being located distally of said reservoir means and having an openable passageway extending therethrough to enable said elongated device to pass through said openable passageway, said valve element comprising a disk-like member formed of a resilient material having a conically-shaped recess, a bore located at the nadir of said recess, and a slit located at the nadir of said recess and extending fully through said disk-like element, wherein the major axis of said valve element is perpendicular to the direction of said slit, wherein said hollow housing is arranged to apply radially inwardly directed pressure to selected portions of the periphery of said valve element, said reservoir means being operative to provide said lubricating fluid onto said elongated device as it passes therethrough to facilitate the passage of said elongated device through said openable passageway in said valve element.

2. The apparatus of claim 1 wherein said reservoir means comprises a urethane foam.

3. The apparatus of claim 2 wherein said lubricating liquid comprises silicone oil.

4. The apparatus of claim 1 wherein said valve element is impregnated with a lubricant.

5. The apparatus of claim 1 wherein said valve element comprises silicone.

6. The apparatus of claim 5 wherein said silicone is impregnated with polydimethylsiloxane.

7. The apparatus of claim 3 wherein said valve element comprises silicone.

8. The apparatus of claim 7 wherein said silicone is treated with polydimethylsiloxane.

9. Apparatus for introducing an elongated device percutaneously into the body of a living being, said apparatus comprising a tubular member having a distal and proximal end portion, said proximal end portion comprising a hollow housing in which hemostatic valve means is located, said hollow housing including a portion of circular shape, said hemostatic valve means comprising reservoir means and a valve element having an oval periphery, said reservoir means having an opening therein through which said elongated device may pass and being formed of a foam material impregnated with a lubricant liquid, said valve element being located distally of said reservoir means and having an openable passageway extending therethrough to enable said elongated device to pass through said openable passageway, said valve element comprising a disk-like member formed of a resilient material having a conically-shaped recess, a bore located at the nadir of said recess, and a slit located at the nadir of said recess and extending fully through said disk-like element, wherein the major axis of said valve element is perpendicular to the direction of said slit, wherein said hollow housing is arranged to apply radially inwardly directed pressure to selected portions of the periphery of said valve element, wherein said selected portions comprises the opposite sides of said slit, said reservoir means being operative to provide said lubricating fluid onto said elongated device as it passes therethrough to facilitate the passage of said elongated device through said openable passageway in said valve element.

10. The apparatus of claim 9 wherein said lubricating liquid comprises silicone oil.

11. The apparatus of claim 1 wherein said valve element comprises silicone.

12. The apparatus of claim 11 wherein said silicone is treated with polydimethylsiloxane.

13. The apparatus of claim 9 wherein said valve element is impregnated with a lubricant.

* * * * *